(12) United States Patent
Helmer

(10) Patent No.: US 11,833,330 B2
(45) Date of Patent: Dec. 5, 2023

(54) PRESSURE SENSOR FOR INJECTION DEVICES

(71) Applicant: SANOFI, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 398 days.

(21) Appl. No.: 16/956,320

(22) PCT Filed: Dec. 19, 2018

(86) PCT No.: PCT/EP2018/086003
§ 371 (c)(1),
(2) Date: Jun. 19, 2020

(87) PCT Pub. No.: WO2019/122027
PCT Pub. Date: Jun. 27, 2019

(65) Prior Publication Data
US 2021/0093785 A1    Apr. 1, 2021

(30) Foreign Application Priority Data

Dec. 20, 2017   (EP) .................................. 17306844

(51) Int. Cl.
*A61M 5/20* (2006.01)
*A61M 5/315* (2006.01)
*A61M 5/31* (2006.01)

(52) U.S. Cl.
CPC .............. *A61M 5/20* (2013.01); *A61M 5/315* (2013.01); *A61M 2005/3128* (2013.01); *A61M 2005/3131* (2013.01); *A61M 2205/3331* (2013.01)

(58) Field of Classification Search
CPC ................... A61M 5/20; A61M 5/315; A61M 2005/3128; A61M 2005/3131; A61M 2205/3331
See application file for complete search history.

(56) References Cited

U.S. PATENT DOCUMENTS

| 5,370,630 A | 12/1994 | Smidebush et al. |
| 2009/0118680 A1* | 5/2009 | Goldbrunner ....... A61M 5/2053 604/236 |

(Continued)

FOREIGN PATENT DOCUMENTS

| WO | WO 2009/024562 | 2/2009 |
| WO | WO 2014/158627 | 10/2014 |
| WO | WO 2018/083062 | 5/2018 |

OTHER PUBLICATIONS

PCT International Preliminary Report on Patentability in International Appln. No. PCT/EP2018/086003, dated Jun. 23, 2020, 8 pages.

(Continued)

*Primary Examiner* — Lauren P Farrar
(74) *Attorney, Agent, or Firm* — Fish & Richardson P.C.

(57) ABSTRACT

The present application relates to pressure sensors for injection devices. According to a first aspect, the specification discloses an injection device comprising: a medicament container comprising medicament container walls and a sealing element; a stopper translatably disposed inside the medicament container; a pressure sensor; and a plunger passing through an axial bore of the sealing element, the plunger being operable to displace the stopper, wherein the sealing element, stopper and medicament container walls define a cavity inside the medicament container; and wherein the pressure sensor is configured to measure the pressure inside the cavity during an injection.

13 Claims, 4 Drawing Sheets

(56) References Cited

U.S. PATENT DOCUMENTS

| | | |
|---|---|---|
| 2014/0094770 A1 | 4/2014 | Li et al. |
| 2014/0288408 A1* | 9/2014 | Deutsch ............. A61M 5/31511 128/207.14 |
| 2019/0167907 A1* | 6/2019 | Faulkner ............. A61M 5/1782 |
| 2019/0262544 A1* | 8/2019 | Richter ............... A61M 5/3155 |

OTHER PUBLICATIONS

PCT International Search Report and Written Opinion in International Appln. No. PCT/EP2018/086003, dated Feb. 12, 2019, 13 pages.

* cited by examiner

PRESSURE SENSOR FOR INJECTION DEVICES

CROSS REFERENCE TO RELATED APPLICATIONS

The present application is the national stage entry of International Patent Application No. PCT/EP2018/086003, filed on Dec. 19, 2018, and claims priority to Application No. EP 17306844.6, filed on Dec. 20, 2017, the disclosures of which are incorporated herein by reference.

TECHNICAL FIELD

The present application relates to pressure sensors for injection devices. In particular, it relates to pressure sensors for monitoring injection times in injection devices.

BACKGROUND

Monitoring a patient's injection regime can provide useful information regarding the patient's compliance with the regime and whether the patient is using their injection equipment correctly. One set of information that can be useful is an indication and/or record that an injection has occurred. Another is the injection duration. This can be indicative of the amount of medication expelled by the injection equipment during the injection. It can also indicate whether the injection device is working properly. This can be particularly important in autoinjector devices.

SUMMARY

According to a first aspect, the specification discloses a medicament delivery device comprising: a medicament container comprising medicament container walls and a sealing element; a stopper translatably disposed inside the medicament container; a pressure sensor; and a plunger passing through an axial bore of the sealing element, the plunger being operable to displace the stopper, wherein the sealing element, stopper and medicament container walls define a cavity inside the medicament cartridge; and wherein the pressure sensor is configured to measure the pressure inside the cavity.

The pressure sensor may be configured to determine an injection duration from measurements of the pressure inside the cavity.

The pressure sensor may be configured to detect a plateau in the measurements of the pressure inside the cavity to determine the injection duration based on the length of the plateau.

The pressure sensor may be configured to detect a start time of the injection and an end time of the injection and to determine the injection duration based on the difference between the start time and the end time.

The pressure sensor may be configured to identify a start of an injection when the pressure within the cavity decreases below a threshold value.

The sealing element may comprise a lip extending from an inner wall of the axial bore for allowing air into the cavity when the negative pressure inside the cavity exceeds a threshold value.

The pressure sensor may be located outside the cavity.

The sealing element may comprise one or more conduits fluidly connecting the cavity to the pressure sensor.

The medicament delivery device may be an autoinjector, the autoinjector comprising a drive mechanism for actuating the plunger.

The plunger may further comprise one or more slits, the slits fluidly connecting the cavity to an external atmosphere when the plunger is in a pre-defined depressed position, for example a defined end of injection position.

The medicament delivery device may further comprise a medicament.

According to a second aspect, the specification also describes a method of determining an injection duration comprising: monitoring air pressure in a cavity of a medicament container using a pressure sensor; determining a start time of an injection event when the pressure measured in the cavity decreases below a first threshold value; determining an end time of an injection event when the pressure measured in the cavity increases above a second threshold value; and determining the injection duration in dependence on the start time and end time of the injection event.

The first threshold value and second threshold value may be identical.

Determining the start time may trigger a timer to start and determining the end time may trigger the timer to stop.

Determining the start time may comprise recording the start time of the injection event; determining the end time may comprise recording the end time of the injection event; and determining the injection duration may comprise taking the difference between the recorded end time and the recorded start time of the injection event.

As used herein, the term medicament delivery device is used to refer to at least any of the following: an injection device; an autoinjector; a pen type injector (disposable or reusable); an infusion device (for example a patch-type infusion device or a belt-worn infusion device with a cable); a "naked" syringe; or a jet injector. The medicament delivery device may administer a medicament as a bolus and/or continuously at a basal rate.

DETAILED DESCRIPTION

Figure 1A:
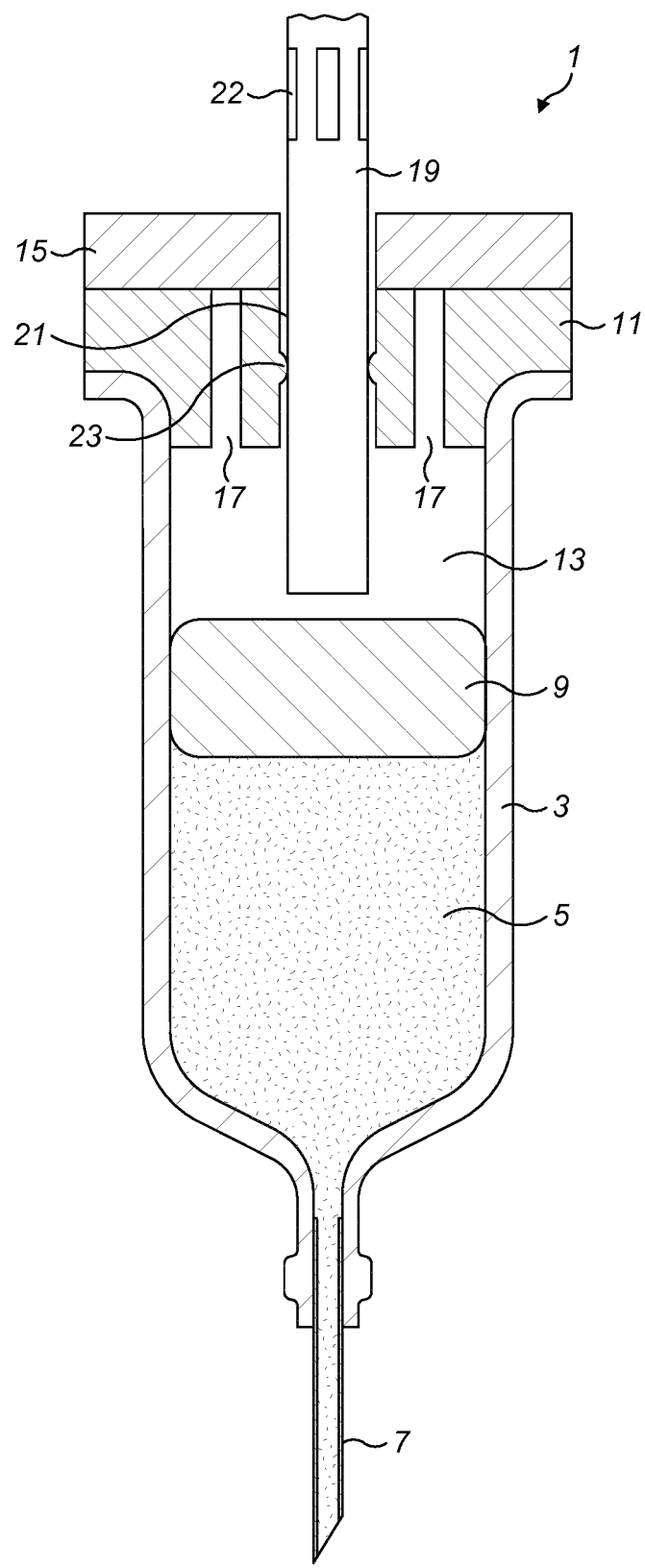
FIG. 1a shows a cross section of an embodiment of a medicament delivery device with a pressure sensor.

FIG. 1 shows a cross section of an embodiment of a medicament delivery device with a pressure sensor.

The medicament delivery device 1 comprises a medicament container 3 for retaining a medicament 5. The medicament container 3, in some embodiments, forms part of a syringe. For example, the medicament container 3 may be a prefilled syringe, as for example used in auto injectors or a prefilled syringe ready for use, as for example used for Novocain. In other embodiments, the medicament container 3 forms a part of an auto-injector. In such cases, the medicament container 3 may be a consumable part of the auto-injector capable of being replaced as required. In the embodiment shown, the walls of the medicament container 3 are substantially cylindrical. The medicament container 3 may be a medicament cartridge, such as a medicament cartridge used for Insulin pen injectors. These may be disposable or reusable.

The medicament delivery device 1 further comprises an outlet 7 via which the medicament 5 can be expelled from the medicament container 3. The outlet 7 is, in some embodiments, in the form of a needle. The needle can be an integral part of the medicament container 3. In other embodiments, the outlet 7 comprises a head portion for receiving a needle, which a separate part. In further embodiments, the medicament delivery device 1 does not use a needle, for example in a patch type injection device.

A stopper 9 is translatably disposed between the walls of the medicament container 3. The stopper 9 is translatable in the axial direction of the medicament container 3.

A sealing element, such as seal 11 is provided at a proximal end of the medicament container 3 to the outlet 7. As used herein, the proximal end of the medicament delivery device 1 and medicament cartridge 3 is the end opposite to the end of the medicament delivery device 1 at which the needle is located. The distal end of the medicament delivery device 1 and medicament container 3 is the end at which the outlet 7 is located.

The stopper 9, seal 11 and medicament cartridge walls define a cavity 13 inside the medicament container 3. The cavity 13 varies in volume in dependence on the position of the stopper 9 within the medicament container 3. The cavity 13 is substantially airtight up to a threshold pressure, as described below.

A pressure sensor 15 is provided to measure the pressure of air within the cavity 13. The pressure sensor 15 can monitor the initiation and/or the duration of an injection event by determining the start point and, in some embodiments, the end point of the injection based on the pressure within the cavity 13, as described below in relation to FIGS. 3 and 4. In the embodiment shown, the pressure sensor 15 is provided outside of the cavity 13. In alternative embodiments it can instead be provided inside the cavity.

The pressure sensor 15 is, in the embodiment shown, provided as a part of the medicament cartridge. However, in some embodiments, it can alternatively be provided as part of the injection device, for example an autoinjector, into which the medicament container 3 is inserted. For example, the pressure sensor, seal and the electronics could be mounted on the primary pack of an autoinjector during final assembly.

In the example shown, the seal 11 is provided with one or more secondary bores 17 that provide at least a part of a conduit that fluidly connects the cavity 13 to the pressure sensor 15 to facilitate the measurement of pressure within the cavity 13. In some embodiments, the pressure sensor 15 is mounted immediately behind the seal 11 and the secondary bores 17 fully provide the conduit. In other embodiments, the pressure sensor 15 may be mounted away from the seal 11, in which case the conduit will extend from the secondary bores 17 to the pressure sensor 15, with the secondary bores 17 providing a part of the conduit.

A plunger 19 passes through the seal 11 and into the cavity 13 via an axial bore 21 in the seal 11. The plunger 19 is displaceable in the axial direction of the medicament container 3. When depressed towards the distal end of the medicament container 3, the plunger 19 acts to displace the stopper 9 towards the outlet 7 (for example the needle), thereby expelling the medicament 5 from the medicament container 3 via the outlet 7. In embodiments using an auto-injector, the plunger 19 is mounted in and/or driven by an auto-injector drive mechanism (also referred to as a powerpack).

Figure 1B:
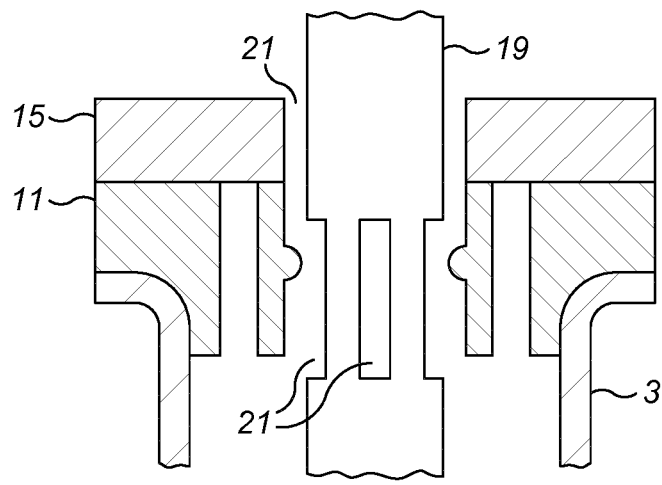
FIG. 1b shows an example of a cross section of part of a medicament delivery device with the plunger depressed.

In some embodiments, the plunger 19 comprises one or more slits 22 on its body. With reference to FIG. 1b, the slits 22 are positioned on the plunger body such that they extend through the axial bore 21 when the plunger 19 is depressed to a predefined position. This fluidly connects the cavity 13 to the air outside the cavity 13. In some embodiments, the slits 22 are positioned to fluidly connect the cavity 13 to the atmosphere outside the cavity 13 when the plunger is fully depressed. In some embodiments, the slits 22 are positioned to fluidly connect the cavity 13 to the atmosphere outside the cavity 13 at a time after the start of the injection has been determined by the pressure sensor 15.

However, referring again to FIG. 1a, the slits 22 are positioned on the plunger body such that when the plunger 19 is not depressed the slits 22 do not extend into the cavity 13, and the cavity 13 is sealed from the outside air.

In some embodiments, the seal 11 is provided with a flexible circumferential lip 23 extending from an inner wall of the axial bore 21. The flexible lip 23 material can be formed from the same material as the seal 11, or be a plastic insert as a separate part. The flexible lip 23 dimension is adjusted to the plunger dimension to realize a substantially optimal gliding friction for the plunger and seal the cavity negative pressure. The flexible lip 23 acts to limit the negative pressure in the cavity 13 to realize the specified injection time and/or prevent stalling. When the negative pressure inside the cavity 13 exceeds a threshold pressure, the flexible lip 23 allows air to enter the cavity 13 to keep the magnitude of the negative pressure at or below the threshold value. In this way, the flexible lip 23 acts like a valve. In some embodiments, other types of valve can be used. For example, a duck-billed valve can alternatively be used.

In use, the plunger 19 is depressed towards the distal end of the medicament container 3. This can be done manually by a user in the case of a syringe, with the user using their fingers to depress the plunger 19. In auto-injector embodiments, the depression of the plunger 19 is achieved automatically, for example using a drive mechanism, such as a spring. The drive mechanism can actuate the plunger 19 to depress the plunger 19 into the cavity 13. In patch type infusion/injection devices, the plunger can be depressed by an electric motor or spring for example.

In either type of embodiment, the depression of the plunger 19 results in the plunger 19 coming into contact with the stopper 9. Further depression of the plunger 19 will result in the stopper 9 being displaced axially along the medicament container 3 towards the outlet 7. This causes medicament 5 in the medicament container 3 to be expelled from the outlet 7.

As the stopper 9 is displaced towards the distal end of the medicament container 3, the volume of the cavity 13 increases. This results in a decrease in negative pressure inside the cavity 13. As the stopper 9 moves further towards the outlet 7, the pressure in the cavity 13 continues to decrease.

The pressure change in the cavity 13 is monitored by the pressure sensor 15. In embodiments where the pressure sensor 15 is outside the cavity, this can be achieved via a conduit comprising secondary bores 17 in the seal 11.

The decrease in pressure in the cavity 13 acts to resist the depression of the plunger 19. This can stall the plunger 19, preventing the expulsion of medicament 5 from the medicament container 3. The flexible lip 23 of the axial bore 21 allows air to flow into the cavity 13 when the pressure in the cavity 13 falls below a threshold value (or equivalently, that the negative pressure is above a threshold value). This prevents the pressure inside the cavity 13 falling much below the threshold value, hence reducing stalling.

Figure 2:
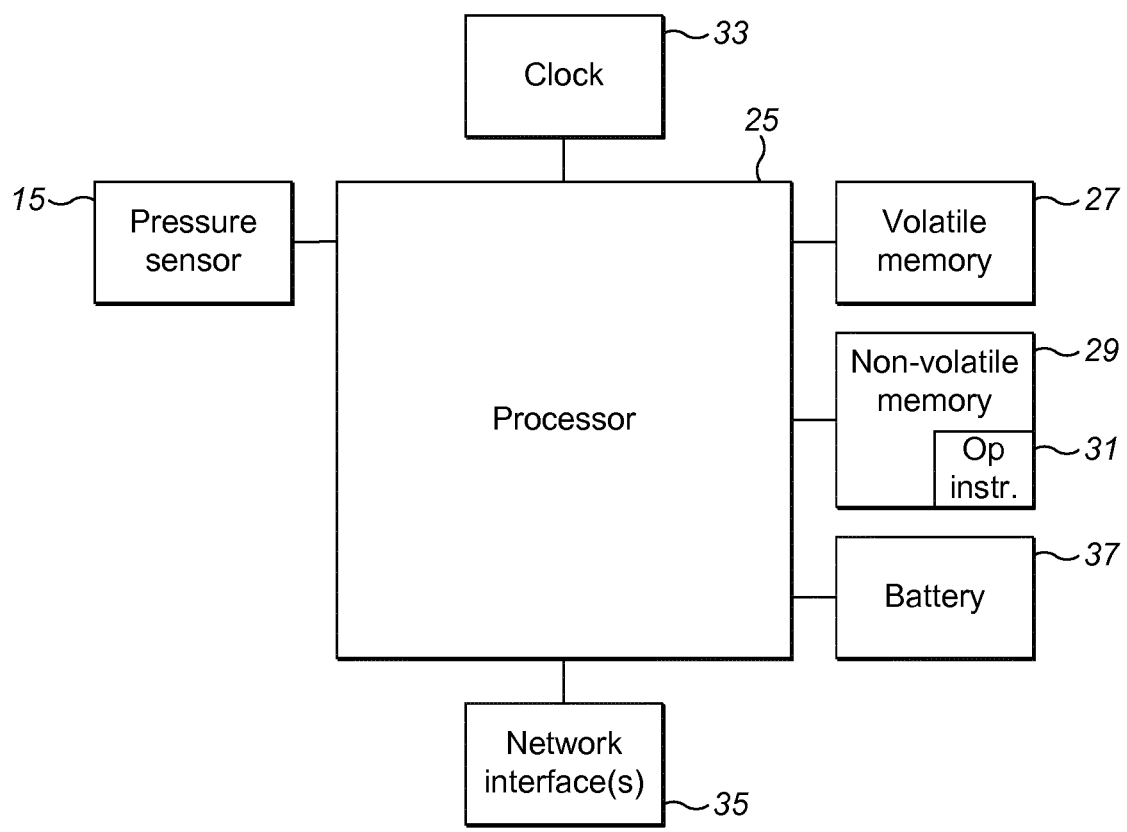
FIG. 2 shows an example of a schematic representation of the electronics system of a pressure sensor.

FIG. 2 shows an example of a schematic representation of the electronics system of a pressure sensor.

As best seen from FIG. 2, the electronics system of the pressure sensor comprises the processor arrangement 25. The processor arrangement 25 and other hardware components may be connected via a system bus (not shown). Each hardware component may be connected to the system bus either directly or via an interface. A power supply is arranged to provide power to the electronics system.

The processor arrangement 25 controls operation of the other hardware components of the electronics system. The processor arrangement 25 may be an integrated circuit of any kind. The processor arrangement 25 may for instance be a general purpose processor. It may be a single core device or a multiple core device. The processor arrangement 25 may be a central processing unit (CPU) or a general processing unit (GPU). Alternatively, it may be a more specialist unit, for instance a RISC processor or programmable hardware with embedded firmware. Multiple processors may be included. The processor arrangement 25 may be termed processing means.

The electronics system comprises a working or volatile memory 27. The processor arrangement 25 may access the volatile memory 27 in order to process data and may control the storage of data in memory. The volatile memory 27 may be a RAM of any type, for example Static RAM (SRAM), Dynamic RAM (DRAM), or it may be Flash memory. Multiple volatile memories may be included, but are omitted from FIG. 2.

The electronics system comprises a non-volatile memory 29. The non-volatile memory 29 stores a set of operation instructions for controlling the normal operation of the processor arrangement. The non-volatile memory 29 may be a memory of any kind such as a Read Only Memory (ROM), a Flash memory or a magnetic drive memory. Other non-volatile memories may be included, but are omitted from FIG. 2.

The processor arrangement 25 operates under the control of the operating instructions 31. The operating instructions 31 may comprise code (i.e. drivers) relating to the hardware components of the electronics system, as well as code relating to the basic operation of the apparatus. The operating instructions 31 may also cause activation of one or more software modules stored in the non-volatile memory 29. Generally speaking, the processor arrangement 25 executes one or more instructions of the operating instructions 31, which are stored permanently or semi-permanently in the non-volatile memory 29, using the volatile memory 27 temporarily to store data generated during execution of the operating instructions.

The processor arrangement 25, the volatile memory 27 and the non-volatile memory 29 may be provided as separate integrated circuit chips connected by an off-chip bus, or they may be provided on a single integrated circuit chip. The processor arrangement 25, the volatile memory 27 and the non-volatile memory 29 may be provided as a microcontroller.

The electronics system comprises a clock 33. The clock 33 may be a clock crystal, for example, a quartz crystal oscillator. The clock 33 may be a separate component to the processor arrangement 25 which is configured to provide a clock signal to the processor arrangement 25. The processor arrangement 25 may be configured to provide a real time clock based on the signal from the clock 33. Alternatively, the clock 33 may be a clock crystal which is provided on a single integrated circuit chip with the processor arrangement 25.

In some embodiments, the electronics system comprises one or more network interfaces 35. The network interfaces 35 facilitate the connection of the apparatus to one or more computer networks and the bi-directional exchange of information between the apparatus and other members of the networks. These networks may include the Internet, a Local Area Network, or any other network required by the apparatus to communicate with the data center and/or contact center. The network interfaces 35 comprise a network interface controller, such as an Ethernet adaptor, a Wi-Fi adaptor and/or a Bluetooth adaptor. The network interfaces 35 are associated with one or more network addresses for identifying the apparatus on the network. The one or more network addresses may be in the form of an IP address, a MAC address, and/or an IPX address. Other members of the network may include medical devices that are collecting user data. The other members of the network may, in some embodiments, be connected to the portable medical data hub through Wi-Fi Protected Setup (WPS).

The electronics system may be provided with a battery 37 to supply power to the pressure sensor 15 and the electronics system.

Figure 3:
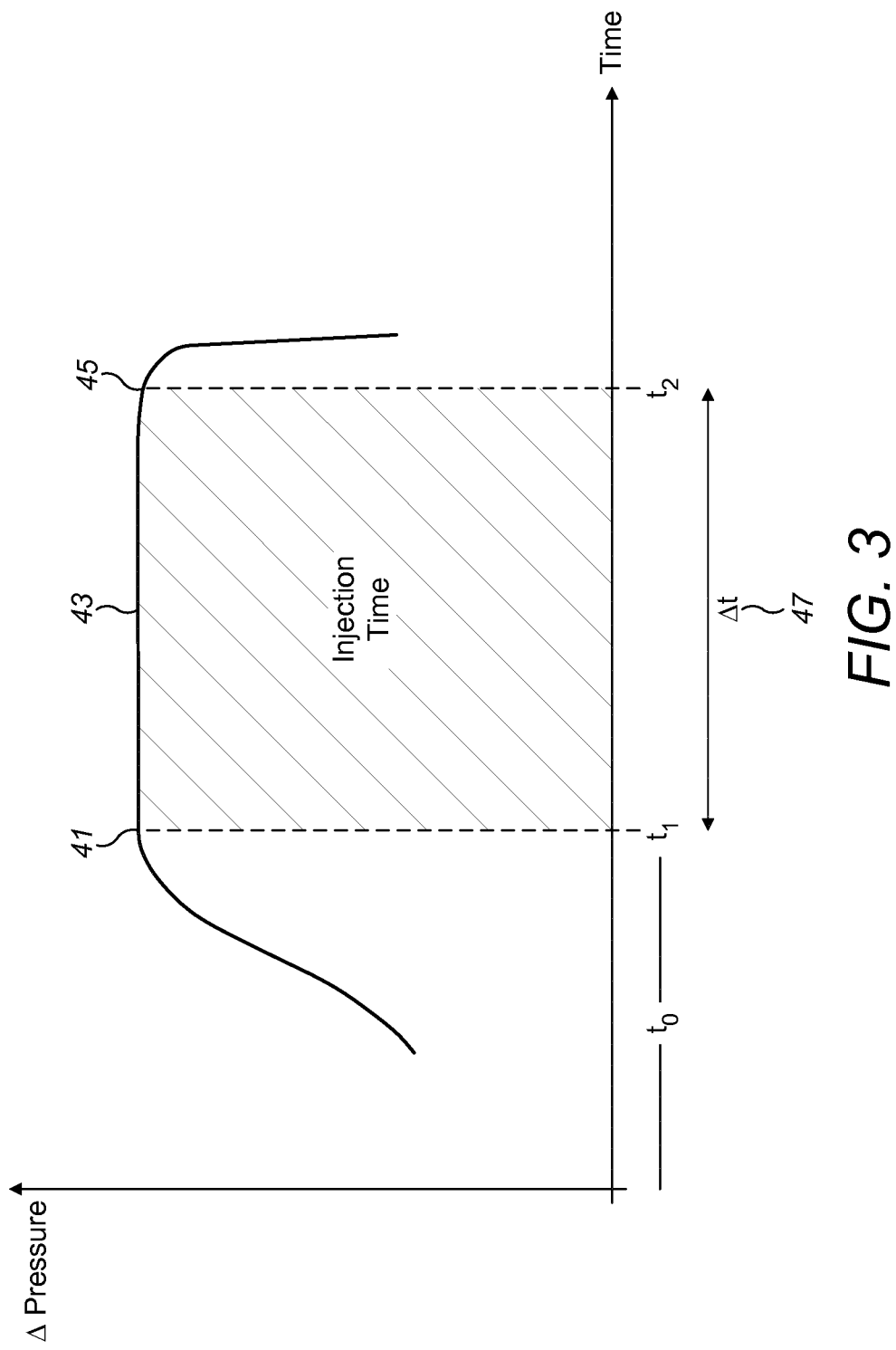
FIG. 3 shows an example of an ideal graph of pressure measured by the pressure sensor during an injection event.

FIG. 3 shows an example of a graph of pressure measured by the pressure sensor during an injection event.

The negative cavity pressure measured by the pressure sensor 15 relative to an initial cavity pressure is shown as a function of time during an injection event. The y-axis shows the magnitude of the cavity pressure change relative to the initial cavity pressure. The x-axis shows time progressing from left to right. It will be appreciated that the increase in the pressure change during the injection event corresponds to a decrease in pressure in the cavity 13. The example shown in FIG. 3 is an ideal example. In reality, the pressure reading obtained by the pressure sensor may have a degree of noise to it. Furthermore, in some examples the "plateau" in the pressure measurement can be saw-toothed due to the action of the flexible lip or valve.

As it is depressed, the plunger 19 begins moving the stopper towards the outlet 7 of the medicament cartridge at time $t_0$, leading to a decrease in pressure in the cavity 13. This is shown on the graph by a rise 39 in the magnitude of the pressure change starting at to.

As the stopper 9 is pushed towards the distal end of the medicament container 3, the pressure in the cavity 13 decreases until it reaches a threshold value 41 at time $t_1$. As the pressure approaches the threshold value, the flexible lip 23 in the axial bore 21 in the seal 11 allows additional air to enter the cavity 13. This maintains the pressure at or near the threshold value, resulting in a plateau 43 in the measured change in pressure as the plunger is depressed further.

As the plunger 19 approaches the end of its stroke at time $t_2$, the slits 22 in the plunger body pass through the axial bore 21, resulting in the cavity 13 becoming fluidly connected to the air outside the cavity 13. This results in pressure compensation in the cavity 13 as air can flow freely into and out of the cavity 13. The pressure in the cavity 13 therefore increases between times $t_2$ and $t_3$ back to its initial value.

In embodiments where the slits 22 in the plunger 19 are located to span the flexible lip 23 or valve when the plunger is fully depressed, the rise in pressure starting at $t_2$ indicates the end of the injection event. In other embodiments, the rise in pressure indicates that the plunger 19 has reached the pre-defined position where the slits 22 span the flexible lip 23 or valve.

Figure 4:
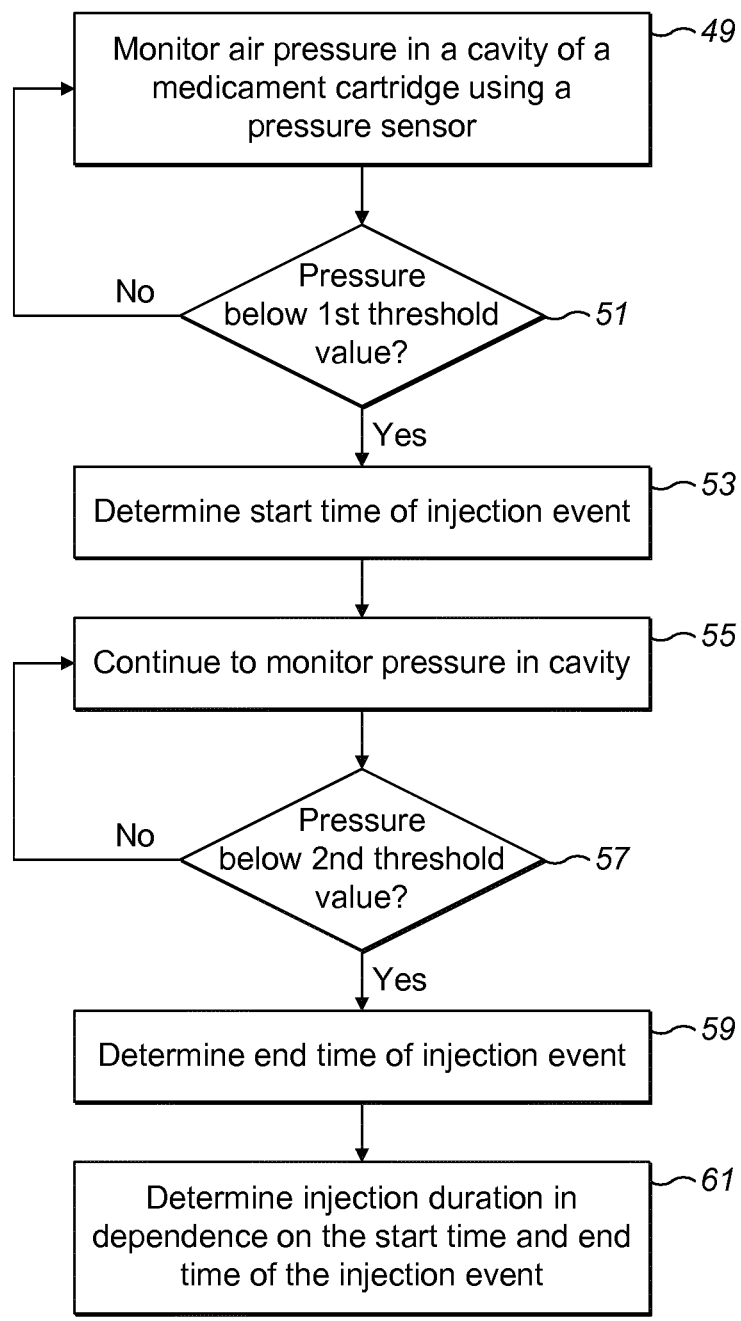
FIG. 4 shows a flow chart of an example of a method of monitoring an injection event.

FIG. 4 shows a flow chart of an example of a method of monitoring an injection event.

At step 49, the pressure in the medicament cartridge cavity 13 is monitored by the pressure sensor 15.

The pressure is monitored to determine if it falls below a threshold value 51. If the pressure has not fallen below the threshold value, then the pressure sensor 15 continues to monitor the pressure in the cavity 13. If the pressure has fallen below the threshold value, at step 53 the time at which it falls below the threshold value is determined to be the start of the injection event.

In some embodiments, the method ends here. The pressure (or equivalently the increase in negative pressure) falling below the threshold value indicates that an injection event has been performed. A date and time of the injection event can then be recorded by the pressure sensor 15 (or its control system).

In some embodiments, the pressure sensor 15 (or its control system) records the time of the start of the injection event. Alternatively or additionally, the detection of the pressure falling below the threshold value triggers the start of a timer.

After determining the start time of the injection event, at step 55 the pressure sensor 15 continues to monitor the pressure in the cavity 13. The pressure sensor 15 checks whether the pressure has risen above a threshold value 57. The checks are performed periodically in some embodiments. Alternatively, the checks are performed continuously by the pressure sensor 15.

In general, the threshold value for determining the start time of the injection event and the threshold value for determining the end time of the injection event do not need to be the same. However, in some embodiments, the threshold values are the same for simplicity.

If the pressure remains below the threshold value, the pressure sensor 15 continues to monitor the pressure in the cavity.

If the pressure rises above the threshold value, then the end time of the injection event is determined 59. In some embodiments, the end time is recorded by the pressure sensor 15 (or its control system). Alternatively or additionally, the pressure in the cavity rising above the threshold value triggers the end of a timer.

In some embodiments, the method detects a plateau in the measurements of the pressure inside the cavity by determining how long the pressure remains between an upper and a lower threshold. The length of the plateau can be used to determine the duration of the injection. In some embodiments, the plateau may be determined using a mathematically derived method.

At step 61, the injection duration is then determined in dependence on the determined start time and end time of the injection event. In embodiments where the start time and end time are recorded, this is achieved by subtracting the start time from the end time. In embodiments where a timer is used, the duration will be determined from the timer reading at the end time. The timer will then be reset for future injection events.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament delivery device comprising:
a medicament container comprising medicament container walls and a sealing element;
a stopper translatably disposed inside the medicament container, wherein the seal element, the stopper, and the medicament container walls define a cavity inside the medicament container;
a pressure sensor; and
a plunger passing through an axial bore of the sealing element, the plunger being operable to displace the stopper, wherein the plunger comprises one or more slits extending along a sidewall of the plunger, wherein the one or more slits fluidly connect the cavity to an external atmosphere when the plunger is at a pre-defined depressed position, and the one or more slits do not extend into the cavity when the plunger is in an undepressed position; and
wherein the pressure sensor is configured to measure a pressure inside the cavity.

2. The medicament delivery device of claim 1, wherein the pressure sensor is configured to determine an injection duration from measurements of the pressure inside the cavity.

3. The medicament delivery device of claim 2, wherein the pressure sensor is configured to detect a plateau in the measurements of the pressure inside the cavity to determine the injection duration based on a length of the plateau.

4. The medicament delivery device of claim 2, wherein the pressure sensor is configured to detect a start time of the injection and an end time of the injection.

5. The medicament delivery device of claim 4, wherein the pressure sensor is configured to determine the injection duration based on a difference between the start time and the end time.

6. The medicament delivery device of claim 1, wherein the pressure sensor is configured to identify a start of an injection when the pressure within the cavity decreases below a first threshold value.

7. The medicament delivery device of claim 6, wherein the pressure sensor is configured to identify an end of the injection when the pressure within the cavity increases above a second threshold value.

8. The medicament delivery device of claim 7, wherein the first threshold value and the second threshold value are identical.

9. The medicament delivery device of claim 1, wherein the sealing element comprises a valve extending from an inner wall of the axial bore configured to allow air into the cavity when the negative pressure inside the cavity exceeds a threshold value.

10. The medicament delivery device of claim 1, wherein the pressure sensor is located outside the cavity.

11. The medicament delivery device of claim 1, wherein the sealing element comprises one or more conduits fluidly connecting the cavity to the pressure sensor.

12. The medicament delivery device of claim 1, wherein the medicament delivery device is an autoinjector, the autoinjector comprising a drive mechanism configured to actuate the plunger.

13. The medicament delivery device of claim 1, wherein the medicament container contains a medicament.

* * * * *